United States Patent [19]

O'Malley et al.

[11] Patent Number: 5,708,007

[45] Date of Patent: Jan. 13, 1998

[54] 2-(PIPERIDIN-4-YL, PYRIDIN-4-YL AND TETRAHYDROPYRIDIN-4-YL) BENZOFURAN-7-OL AND CARBAMATE DERIVATIVES FOR TREATING MEMORY DYSFUNCTION

[75] Inventors: Gerard J. O'Malley, Newtown, Pa.; Udo Hedtmann, Frankfurt, Germany

[73] Assignee: Hoechst Marion Roussel, Inc., Cincinnati, Ohio

[21] Appl. No.: 703,843

[22] Filed: Aug. 27, 1996

Related U.S. Application Data

[63] Continuation of Ser. No. 102,681, Aug. 5, 1993, abandoned.

[51] Int. Cl.$^6$ .................. A61K 31/445; A61K 31/44; C07D 405/04
[52] U.S. Cl. .................. 514/320; 514/337; 546/196; 546/269
[58] Field of Search .................. 546/196, 269; 514/320, 337

[56] References Cited

U.S. PATENT DOCUMENTS

| 4,210,655 | 7/1980 | Schenker | 546/196 |
| 4,600,719 | 7/1986 | Schenker | 546/196 |

FOREIGN PATENT DOCUMENTS

| 0006524 | 6/1979 | European Pat. Off. . |
| 0165810 | 6/1985 | European Pat. Off. . |
| 0217530 | 8/1986 | European Pat. Off. . |
| 0259621 | 8/1987 | European Pat. Off. . |
| 0296560 | 6/1988 | European Pat. Off. . |
| 0338782 | 4/1989 | European Pat. Off. . |
| 0398413 | 5/1990 | European Pat. Off. . |
| 0468187 | 6/1991 | European Pat. Off. . |
| 0542671 | 10/1992 | European Pat. Off. . |
| 1465581 | 2/1977 | United Kingdom . |
| 1565055 | 4/1980 | United Kingdom . |

OTHER PUBLICATIONS

Schenker et al. Chemical Abstract, (72063d) vol. 90, 1979.
Wyngaarden, et al., Textbook of Medicine,. p. 39 (1983).
Wilbraham, et al. Organic and Biological Chemistry, South IL Univ (Publisher) pp. 268–169.
Chen, et al. J. Med Chemistry, "Synethese, Resolution, and Structure–Activity of Potent Acetylcholinesterase Inhibitors 8–Carbaphysostigime Analogue", vol. 35, No. 8, pp. 1429–1434, 1992.
Stern, et a.l. Neurology, "Long–term Administration of oral physostigmine in Alzheimer's Disease", vol. 38, pp. 1837–1841m 1968.
Becker et al Drug Devel Res "Effects of Metrifonate, A Long–Acting Cholinesterase Inhibitor, in Alzheimer Disease: Report of an OpenTrial", 19:425–434, 1990.
Schenker et al "Piperidine Derivatives" CA 90:72063 (1979).
Wyngaarden et al "Cecil Textbook of Medicine" Saunders Co. p. 639 (1983).
Wilbraham et al "Organic and Biological Chemistry" South Ill. University (Publisher), pp. 268–269 (1985).

*Primary Examiner*—Ceila Chang
*Attorney, Agent, or Firm*—J. Michael Dixon

[57] ABSTRACT

These are disclosed novel 2-(piperidin-4-yl, pyridin-4-yl and tetrahydropyridin-4-yl)benzofuran-7-ol and carbamate derivatives of the formula

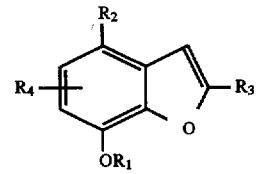

where the substituents are as defined in the specification, which are useful as acetylcholinesterase inhibitors and as such may be useful for the treatment of Alzheimer's disease and other senile dementias.

13 Claims, No Drawings

2-(PIPERIDIN-4-YL, PYRIDIN-4-YL AND TETRAHYDROPYRIDIN-4-YL) BENZOFURAN-7-OL AND CARBAMATE DERIVATIVES FOR TREATING MEMORY DYSFUNCTION

This is a continuation of application Ser. No. 08/102,681, filed Aug. 5, 1993, which is herein incorporated by reference.

The present invention relates to compounds of the general formula

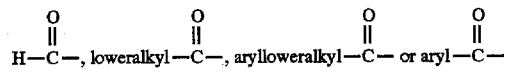

wherein $R_1$ is hydrogen, loweralkyl, arylloweralkyl, $CONHR_{11}$ or $CONR_6R_7$ $R_2$ is hydrogen, cyano, $CH_2NR_8R_9$, $CONHR_5$ or $CONR_6R_7$;

$R_3$ is

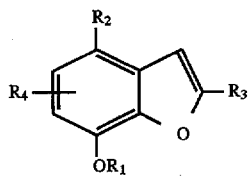

where $R_{10}$ is hydrogen, loweralkyl, arylloweralkyl, $CONHR_5$, $CONR_6R_7$, acyl, acyloxyloweralkyl or acyloxyarylloweralkyl;

$R_4$ is hydrogen, halogen, loweralkyl or loweralkoxy;

$R_5$ is hydrogen, loweralkyl or arylloweralkyl;

$R_6$ is loweralkyl or arylloweralkyl;

$R_7$ is loweralkyl or arylloweralkyl;

$R_8$ is hydrogen, loweralkyl, arylloweralkyl or acyl;

$R_9$ is hydrogen, loweralkyl or arylloweralkyl;

$R_{11}$ is loweralkyl, aryl or arylloweralkyl;

with the proviso that if $R_1$ is hydrogen or loweralkyl, $R_2$ cannot be hydrogen;

or a pharmaceutically acceptable acid addition salt thereof, or, where applicable, an optical or geometric isomer or racemic mixture thereof.

Additionally, this invention also relates to novel intermediates encompassed by the above formula, to pharmaceutical compositions containing said compounds and to their use as acetylcholinesterase inhibitors.

Unless otherwise stated or indicated, the following definitions shall apply throughout the specification and appended claims.

The term "lower" shall mean the group it is describing contains from 1 to 6 carbon atoms.

The term loweralkyl shah mean a straight or branched alkyl group having from 1 to 6 carbon atoms, e.g., methyl, ethyl, n-propyl, isopropyl, n-butyl, isobutyl, sec-butyl, t-butyl and straight and branched chain pentyl and hexyl.

The term halogen shall mean fluorine, chlorine, bromine or iodine.

The term aryl shall mean a phenyl group substituted with 0, 1 or 2 substituents each of which is independently loweralkyl, loweralkoxy, halogen, trifluoromethyl or nitro.

The term acyl shall mean a group of the formula

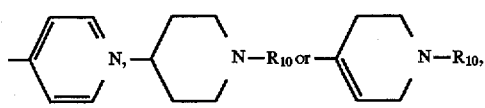

where loweralkyl and aryl are as defined above.

Throughout the specification and appended claims, a given chemical formula or name shall encompass all stereo and optical isomers where such isomers exist.

Additionally, a given chemical formula or name shall encompass the pharmaceutically acceptable addition salts thereof.

In a preferred embodiment of this invention are compounds of the formula

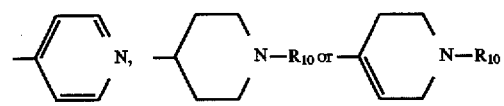

where $R_1$ is $CONHR_{11}$ or $CONR_6R_7$;

$R_2$ is $CH_2NR_8R_9$, $CONHR_5$ or $CONR_6R_7$;

$R_3$ is

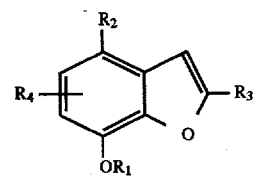

where $R_{10}$ is hydrogen or loweralkyl;

$R_4$ is hydrogen or halogen;

$R_5$ is hydrogen or loweralkyl;

$R_6$ is loweralkyl;

$R_7$ is loweralkyl;

$R_8$ is hydrogen or loweralkyl;

$R_9$ is hydrogen or loweralkyl; and $R_{11}$ is loweralkyl, aryl or arylloweralkyl.

Preferred intermediates of this invention are compounds wherein $R_1$ is loweralkyl;

$R_2$ is cyano, $CH_2NR_8R_9$ or $CONR_6R_7$;

$R_3$ is

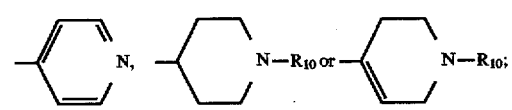

$R_4$ is hydrogen;

$R_5$ is loweralkyl; and $R_6$, $R_7$, $R_8$, $R_9$ and $R_{10}$ are loweralkyl.

The compounds of this invention are prepared in the following manner. The substituents $R_1$ to $R_{11}$ are as defined above unless indicated otherwise.

The compounds of this invention can be prepared according to either of the following synthetic routes.

SYNTHETIC ROUTE I

A carboxylic acid of the formula

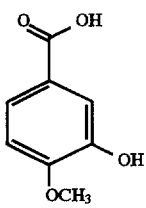

is reacted with thionyl chloride, in a suitable solvent such as toluene, and subsequently reacted with a secondary amine of the formula $HNR_8R_9$, where $R_8$ and $R_9$ are loweralkyl, to yield compound (II) of the formula

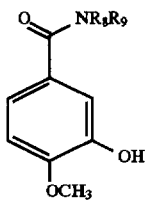

(II)

Compound II is reacted in chloromethyl methyl ether with 50% NaOH in dichloromethane with tetrabutylammonium chloride to afford compound III of the formula

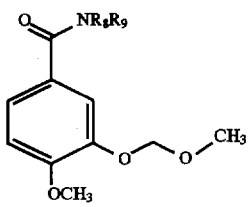

(III)

Compound III in THF is subsequently reacted with sec-butyllithium in a suitable solvent such as cyclohexane, and dimethylformamide is added later to afford compound IV of the formula

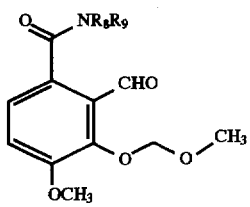

(IV)

where $R_8$ and $R_9$ are ethyl. This reaction is typically conducted at a temperature of $-70°$ to $-40°$ C. for 1 to 4 hours.

Compound IV is hydrolyzed by standard means to afford compound IVa of the formula

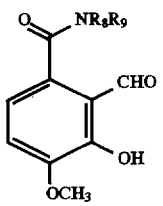

(IVa)

Compound IVa is reacted with 4-picolylchloride hydrochloride, potassium carbonate and a catalyst such as potassium iodide to yield Compound V of the formula

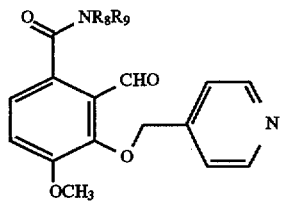

(V)

This reaction is typically conducted in a suitable solvent such as dimethylformamide. The reaction mixture is stirred at about $60°-100°$ C. for 1-3 hours and then heated to about $130°-170°$ C. for 10-30 minutes.

Compound VI of the formula

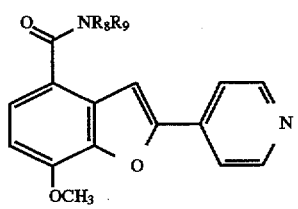

(VI)

was concomitantly formed in the synthesis of Compound V, and the two compounds were chromatographically separated.

Compound VI is subsequently reacted with methyl iodide in methylethyl ketone or other suitable solvent at a temperature of about $40°$ to $60°$ C. to yield Compound VIa of the formula

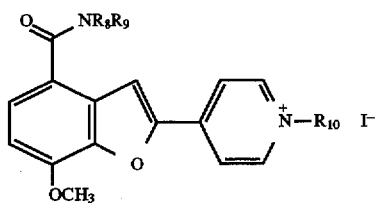

(VIa)

where R10 is methyl. Compound VIa is then treated with a reducing agent such as sodium borohydride or another metallic borohydride in a loweralkanolic solvent such as methanol to give Compound VIb of the formula

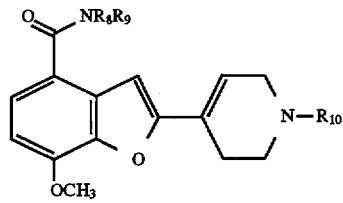

(VIb)

where R10 is methyl. This reaction typically takes place at a temperature of about $-10°$ to $100°$ C. for 0.5 to 24 hours.

Compound VIb is subsequently hydrogenated in the presence of a noble metal catalyst and an acid such as hydrogen bromide to prepare compound VII of the formula

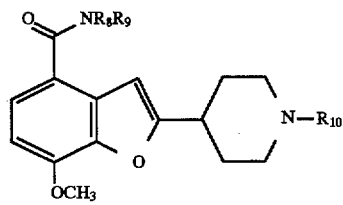

(VII)

where R10 is methyl. Preferred noble metal catalysts include palladium, platinum or rhodium. Platinum, in this case, is preferred; in the form of the metal supported on an inert surface such as carbon or as the oxide or salt.

Compound VII is then treated with a reducing agent such as lithium aluminum hydride to yield compound VIII of the formula

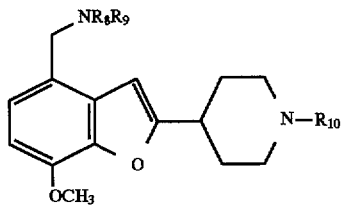 (VIII)

where R10 is methyl. This reaction typically takes place in a suitable solvent such as tetrahydrofuran at a temperature of about 40° to 60° C. for 2 to 4 hours.

Compound VIII is treated with a strong acid, such as 48% HBr, to yield compound IX of the formula

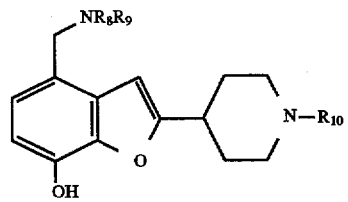 (IX)

where $R_{10}$ is methyl.

Compound IX is subsequently mixed with a catalytic amount of a catalyst such as CuCl or 1,8-diazabicyclo[5.4.0]undec-7-ene (DBU) in a suitable solvent such as dimethylformamide to which is added an isocyanate of the formula $R_{11}NCO$, where $R_{11}$ is loweralkyl, aryl or arylloweralkyl or a carbamoyl chloride of the formula $ClCONR_6R_7$ to afford compound X of the formula

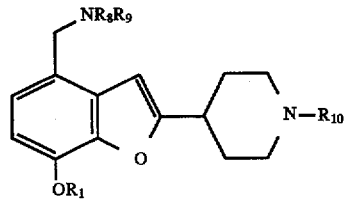 (X)

where $R_1$ is $CONHR_{11}$ or $CONR_6R_7$. This reaction typically takes place under a nitrogen atmosphere at ambient temperature for 12 to 20 hours.

SYNTHETIC ROUTE II

Alternatively, the compounds of this invention can be prepared according to the following synthetic route.

A solution of o-vanillin of the formula

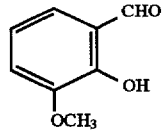

and picolylchloride hydrochloride is reacted with potassium carbonate and potassium iodide in a suitable solvent such as dimethylformamide to afford compound XI of the formula

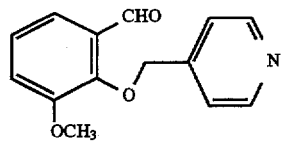 (XI)

Compound XI is subsequently cyclized by reaction with $H_2SO_4$ to afford Compound XII of the formula

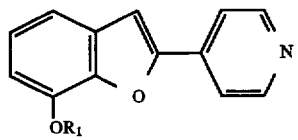 (XII)

Typically, this reaction takes place in a suitable solvent such as DMF at a temperature of about 120° to 170° C. for 6 to 10 hours. Compound XII, where $R_1$ is loweralkyl, can be reacted with a strong acid such as hydrogen bromide at reflux to prepare compound XIIa.

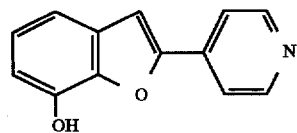 (XIIa)

Compound XIIa is subsequently reacted with an isocyanate of the formula $R_{11}NCO$, where $R_{11}$ is as defined in the previous synthetic route, to afford compound XIII of the formula

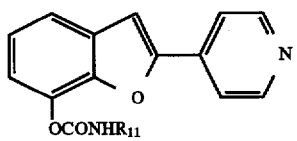 (XIII)

This reaction typically takes place in the presence of a catalytic amount of a metallic halide, such as CuCl or DBU, and ethyl acetate at ambient temperature under nitrogen or other inert gas.

Compound XII, where $R_1$ is loweralkyl, is reacted as shown in the previous synthetic route to afford the piperidinyl compounds of the formula

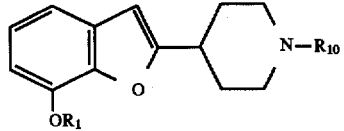 (XIV)

Compound XIV is reacted as previously shown to prepare compounds XIVa and XIVb where $R_1$ is hydrogen and $CONHR_{11}$, respectively.

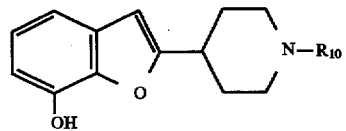 (XIVa)

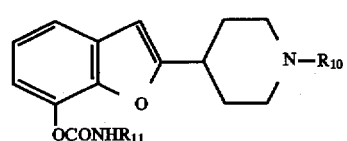 (XIVb)

Alternatively, Compound XIVa can also be reacted with a bicyclic amidine catalyst, such as DBU, with the subsequent addition of an isocyanate of the formula $R_{11}NCO$ to afford compound XIVb. This reaction is typically conducted in a suitable solvent such as acetonitrile under nitrogen at ambient temperature for 2 to 5 hours.

Compound XIV, where $R_1$ is loweralkyl, is reacted with chlorosulfonylisocyanate under nitrogen to afford Compound XV of the formula

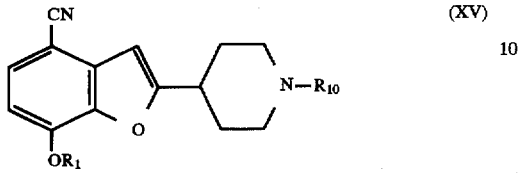

This reaction typically takes place in a suitable solvent such as dichloromethane at room temperature. The reaction mixture is stirred at ambient temperature for 1 to 5 hours and a small porition of dimethylformamide is added and stirring is continued for 12–18 hours.

Compound XIVb, where R10 is methyl, is reacted with chloroethyl chloroformate in a suitable solvent such as dichloroethane and refluxed for 1 to 12 hours. The mixture is concentrated, then diluted with an alkanolic solvent, such as methanol, and refluxed from 1 to 4 hours to yield compound XIVc of the formula

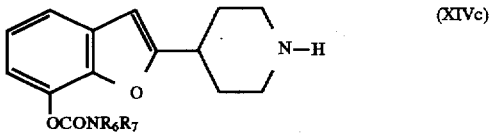

Compound XV is treated with lithium aluminum hydride under a nitrogen atmosphere to yield Compound XVI of the formula

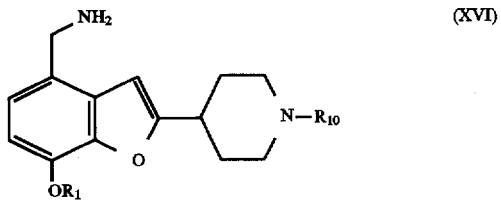

This reaction typically takes place in a suitable solvent such as tetrahydrofuran at ambient temperature for 2 to 6 hours.

Compound XVI can then be treated with a loweralkyl halide or diloweralkyl sulfate to afford Compound XVII of the formula

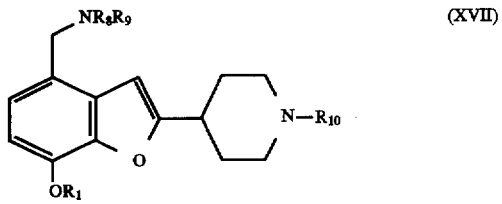

where $R_8$ is loweralkyl and $R_9$ is hydrogen or loweralkyl.

The compounds of the present invention are useful as acetylcholinesterase inhibitors and as such may be useful for the treatment of various memory dysfunctions characterized by a decreased cholinergic function such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum according to the method described below.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

Procedure:

A. Reagents 1. 0.05M Phosphate buffer, pH 7.2
   (a) 6.85 g $NaH_2PO_4 \cdot H_2O/100$ ml distilled $H_2O$
   (b) 13.40 g $Na_2HPO_4 \cdot 7H_2O/100$ ml distilled $H_2O$
   (c) add (a) to (b) until pH reaches 7.2
   (d) Dilute 1:10
2. Substrate in buffer
   (a) 198 mg acetylthiocholine chloride (10 mM)
   (b) bring to 100 ml with 0.05M phosphate buffer, pH 7.2 (reagent 1)
3. DTNB in buffer
   (a) 19.8 mg 5,5-dithiobisnitrobenzoic acid (DTNB) (0.5 mM)
   (b) bring to 100 ml with 0.05M phosphate buffer, pH 7.2 (reagent 1)
4. A 2 mM stock solution of the test drug is made up in a suitable solvent and brought to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2, using a Potter-Elvehjem homogenizer. A 25 microliter aliquot of the homogenate is added to 1 ml of vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)

Program #6 Kindata:

Source—Vis

Wavelength—412 nm

Sipper—none

Cuvettes—2 ml cuvettes using auto 6-sampler

Blank—1 for each substrate concentration

Interval time—15 seconds (15 or 30 seconds for kinetics)

Total time—5 minutes (5 or 10 minutes for kinetics)

Plot—yes

Span—autoscale

Slope—increasing

Results—yes (gives slope)

Factor—1

Reagents are added to the blank and sample cuvettes as follows:

Blank: 0.8 ml Phosphate Buffer/DTNB
0.8 ml Buffer/Substrate

Control: 0.8 ml Phosphate Buffer/DTNB/Enzyme
0.8 ml Phosphate Buffer/Substrate

Drug: 0.8 ml Phosphate Buffer/DTNB/Drug/Enzyme
0.8 ml Phosphate Buffer/Substrate Blank values are determined for each run to control non-enzymatic hydrolysis of substrate and these values are automatically subtracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration $$\% \text{ Inhibition} = \left( \frac{\text{slope control} - \text{slope drug}}{\text{slope control}} \right) (100)$$

$IC_{50}$ values are calculated from log-probit analysis. Results of this assay for some of the compounds of this invention and a reference compound are presented below in Table 1.

TABLE 1

| Compound | Inhibitory Concentration (µM) Brain AChE |
|---|---|
| 2-(1-methyl-4-piperidinyl)-benzofuran-7-yl methyl carbamate | 1.8 |
| 2-(4-pyridinyl)benzofuran-7-yl methyl carbamate | 1.2 |
| 2-(4-piperidinyl) benzofuran-7-yl dimethyl carbamate hemifumarate | 1.9 |
| Physostigmine (reference) | 0.006 |

These compounds are administered to a subject who may benefit from the administration of acetylcholinesterase inhibitors at an effective oral, parenteral or intravenous dose of from about 1 to 100 mg/kg of body weight per day. A particularly preferred effective amount is about 10 mg/kg of body weight per day. It is to be understood, however, that for any particular subject, specific dosage regimen should be adjusted according to the individual need and the professional judgment of the person administering or supervising the administration of the compound. It is to be further understood that the dosages set forth herein are exemplary only and do not to any extent limit the scope or practice of the invention.

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel™, corn starch and the like; a lubricant such as magnesium stearate or Sterotex®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of possible pharmaceutical formulations such as tablets, suppositories and emulsions are described below:

PHARMACEUTICAL FORMULATIONS

TABLET:

| Ingredients | In each tablet |
| --- | --- |
| Active ingredient | 300 mg |
| Polyvinylpyrrolidone | 22.5 mg |
| Lactose | 61.75 mg |
| Alcohol 3A - 200 proof | 4.5 mg |
| Stearic acid | 9 mg |
| Talc | 13.5 mg |
| Corn starch | 43.25 mg |

Blend the active compound, polyvinylpyrrolidone and lactose together and pass through a 40-mesh screen. Add the alcohol slowly, knead well; screen the wet mass through a 4-mesh screen and dry the granulation at 50° C. overnight. Screen the dried granulation through a 20-mesh screen. Bolt the stearic acid, talc and corn starch through a 60-mesh screen prior to mixing by tumbling with the granulation. Compress using 7/16 in. standard concave punch. 10 tablets should weigh 4.5 g.

SUPPOSITORY:

| Ingredients | In each suppository |
| --- | --- |
| Active ingredient | 300 mg |
| Glycerin | 3000 mg |
| Purified water | 200 mg |

The glycerin is heated in a suitable container to about 120° C. The drug is dissolved, with gentle stirring, in the heated glycerin after which the purified water is added, mixed and the hot mixture immediately poured into a suitable mold.

EMULSION:

| Ingredients | Amount |
| --- | --- |
| Gelatin Type A* | 4 g |
| Active Ingredient | 360 mg |
| Flavor as desired | |
| Alcohol | 30 ml |
| Oil | 250 ml |
| Purified water, to make | 500 ml |

*prepared from acid-treated precursors; used at a pH of ca. 3.2.

Add the gelatin and the drug to about 300 ml of purified water, allow to stand for a few minutes, heat until the gelatin is dissolved, then raise the temperature to about 98° C., and maintain this temperature for about 20 min. Cool to 50° C., add the flavor, the alcohol, and sufficient purified water to make 500 ml. Add the oil, agitate the mixture thoroughly, and pass it through a homogenizer or a colloid mill until the oil is completely and uniformly dispersed.

Examples of the compounds of this invention include:
N,N-Diethyl-2-formyl-4-methoxy-3-(methoxymethylenoxy)benzamide;
N,N-diethyl-4-methoxy-2-formyl-3-(4-pyridinylmethoxy)benzamide;
4-(N,N-diethyl)-7-methoxy-2-(4-pyridinyl)benzofuranamide;
1-methyl-4-(4-N,N-diethylamido-7-methoxy-2-benzofuranyl)piperidinium maleate;
1-methyl-4-(4-cyano-7-methoxy-2-benzofuranyl)piperidinium maleate;
1-methyl-4-(4-aminomethyl-7-methoxy-2-benzofuranyl)piperidine dihydrobromide;
1-methyl-4-(4-N,N-diethylaminomethyl-7-methoxy-2-benzofuranyl)piperidine dihydrobromide monohydrate;
2-(1-methyl-4-piperidinyl)-benzofuran-7-yl methyl carbamate;
2-(4-pyridinyl)benzofuran-7-yl methyl carbamate;
2-(4-pyridinyl)benzofuran-7-yl butyl carbamate;
Methyl-4-(7-methoxy-2-benzofuranyl)piperidine;
1-methyl-4-(4-N,N-dimethylamino-7-methoxy-2-benzofuranyl)piperdine;
2-(1-methyl-4-piperidinyl)benzofuran-7-yl 1,2,3,4-tetrahydroisoquinolyl carbamate;
2-(4-pyridinyl)-4-N,N-diethylaminobenzofuran-7-yl methyl carbamate;
2-(1-methyl-4-piperidinyl)-4-N,N-dimethylamino-2-benzofuran-7-yl butyl carbamate; and
2-(4-piperidinyl)benzofuran-7-yl dimethyl carbamate.

The following examples are for illustrative purposes and are not to be construed as limiting the invention disclosed therein. All temperatures are given in degrees centigrade (°C.) unless indicated otherwise.

EXAMPLE 1

N,N-DIETHYL-2-FORMYL-4-METHOXY-3-(METHOXYMETHYLENOXY)BENZAMIDE

To a solution of N,N-diethyl-4-methoxy-3-(methoxymethyleneoxy)benzamide (82.0 g) in tetrahydrofuran (hereafter "THF") (800 ml) at −55° C. was added a 1.3M solution of sec-butyl lithium in cyclohexane (307 ml) dropwise during 1 hour. After stirring the mixture for an additional hour at −55° C., dimethylformamide (hereafter "DMF"), (36.5 g) was added dropwise. The mixture was allowed to warm to ambient temperature and stirred for 2 hours, poured into ice cold 5% HCl, and extracted twice with ethyl acetate. The combined organic phases were washed with water and brine, dried ($Na_2SO_4$) and concentrated in vacuo to give 97g of crude product. Preparative high performance liquid chromatography (silica gel, eluting with 1:2 heptane:ethyl acetate) afforded 58 g of the pure product which was crystallized from heptane/acetone, m.p. 75°–77° C.

Analysis: Calculated for $C_{15}H_{21}NO_5$: 61.00% C 7.17% H 4.74% N Found: 60.97% C 7.12% H 4.84% N

EXAMPLE 2a

N,N-DIETHYL -4-METHOXY-2-FORMYL-3-(4-PYRIDINYLMETHOXY)BENZAMIDE

A suspension of N,N-diethyl-4-methoxy-3-(4-pyridinylmethoxy)benzamide (19.0 g), 4-picolylchloride hydrochloride (15.0 g), $K_2CO_3$ (60.0 g) and potassium iodide (5.0 g) in DMF (500 mol) was stirred at 80° C. for 2 hours and then heated to 150° C. for 15 minutes. After cooling to room temperature, the mixture was poured into 3 l of water, and extracted twice with ethyl acetate. The combined organic phases were washed with 5% $Na_2CO_3$, dried ($Na_2SO_4$) and concentrated in vacuo. High performance liquid chromatography (silica gel, eluting with 1:1 heptane:ethyl acetate) afforded 6.5 g of the product which was crystallized from heptane/acetone, m.p. 117°–118° C.
Analysis: Calculated for $C_{19}H_{22}N_2O_4$ 66.65% C 6.48% H 8.18% N Found: 66.56% C 6.64% H 8.12% N

EXAMPLE 2b

4-(N,N-DIETHYL)-7-MEHOXY-2-(4-PYRIDINYL) BENZOFURANAMIDE

The named compound was produced during the reaction leading to the formation of the N,N,-diethyl-4-methoxy-2-formyl-3-(4-pyridinylmethoxy)benzamide and was isolated in pure form in the chromatography step. Crystallization from heptane/acetone afforded 2.8 g of the named compound, m.p. 115°–117° C.
Analysis: Calculated for $C_{19}H_{20}N_2O_3$: 70.35% C 6.21% H 8.64% N Found: 69.97% C 6.30% H 8.48% N

EXAMPLE 3

1-METHYL-4-(4-N,N-DIETHYLAMIDO-7-METHOXY-2-BENZOFURANYL)PIPERIDINIUM MALEATE

A mixture of 4-(N,N-diethyl)-7-methoxy-2-(4-pyridinyl) benzofuranamide (4.3 g), methyl iodide (2.55 g) and 2-butanone (30 ml) was stirred at 50° C. for 15 hours. The mixture was cooled to 0° C., filtered and the resulting solid was washed with cold 2-butanone and heptane to give 4-[2-(4-diethylamido-7-methoxy-2-benzofuranyl)]-1-methyl pyridinium iodide. The quaternary salt (6.0 g) was dissolved in methanol (100 ml) and a solution of $NaBH_4$ (5.0 g) in $H_2O$ (20 ml) was added dropwise over 30 minutes. The mixture was stirred at ambient temperature for 16 hours, concentrated and the residual aqueous layer was extracted with dichloromethane (hereinafter "DCM"). The DCM extracts were combined, washed with brine and concentrated to give N,N-diethyl-7-methoxy-2-(1-methyl-1,2,3-6-tetrahydro-4-pyridinyl)benzofuranamide.

To a solution of N,N-diethyl-7-methoxy-2-(1-methyl-1,2, 3,6-tetrahydro-4-pyridinyl)benzofuranamide (4.4 g) in methanol (120 ml) and 48% HBr (2.1 g) was added $PtO_2$ (160 mg) and the mixture was hydrogenated in a Parr Shaker for 6 hours at room temperature. The mixture was filtered and the methanol was evaporated in vacuo. The residual solution was treated with 2N $NH_4OH$ and extracted twice with DCM. The combined organic phases were washed with brine, dried ($Na_2SO_4$) and concentrated in vacuo. Flash chromatography (silica gel, eluting with 5% MeOH/DCM containing 0.1% $NH_4OH$) afforded 2.1 g of product which was converted to the maleic acid salt in ethereal solution, m.p. 123°–125° C.
Analysis: Calculated for $C_{24}H_{32}N_2O_7$: 62.59% C 7.00% H 6.08% N Found: 61.76% C 6.94% H 5.79% N

EXAMPLE 4

1-METHYL-4-(4-CYANO-7-METHOXY-2-BENZOFURANYL)PIPERIDINIUM MALEATE

To a solution of 1-methyl-4-(7-methoxy-2-benzofuranyl) piperidine (2.45 g) in anhydrous DCM under nitrogen was added chlorosulfonylisocyanate (2.2 g) dropwise via syringe at room temperature. The mixture was stirred at ambient temperature for 3 hours, then DMF (0.5 ml) was added, and the mixture was stirred for 15 hours. The reaction mixture was poured into water, and extracted twice with DCM. The combined organic phases were washed with brine, dried ($Na_2SO_4$) and concentrated in vacuo. Flash chromatography (silica gel eluting with 5% MeOH/DCM containing 0.01% $NH_4OH$) afforded 1.55 g of product which was converted to the maleic acid salt in ethereal solution, m.p. 175°–177° C.
Analysis: Calculated for $C_{20}H_{22}N_2O_6$: 62.17% C 5.74% H 7.25% N Found: 61.87% C 5.75% H 7.03% N

EXAMPLE 5

1-METHYL-4-(4-AMINOMETHYL-7-METHOXY-2-BENZOFURANYL)PIPERIDINE DIHYDROBROMIDE

To 1-methyl-4-(4-cyano-7-methoxy-2-benzofuranyl) piperidine (2.7 g) in anhydrous THF under nitrogen was added $LiAlH_4$ (30 ml of a 1M solution in THF) dropwise at room temperature. The mixture was stirred at ambient temperature for 4 hours, and then water (2.0 ml) was added slowly under ice cooling. The precipitate was filtered and washed with ethyl acetate. The combined filtrates were dried ($Na_2SO_4$) and concentrated in vacuo to give 2.3 g of the crude product. Flash chromatography (silica gel, eluting with 20% MeOH/DCM+0.1% $NH_4OH$) afforded the product, which was converted to the dihydrobromide salt in ethereal solution, m.p. 195° C. (dec.).
Analysis: Calculated for $C_{16}H_{24}Br_2NO_2$: 44.06% C 5.55% H 6.42% N Found: 43.74% C 5.66% H 6.17% N

EXAMPLE 6

1-METHYL-4-(4-N,N-DIETHYLAMINOMETHYL-7-METHOXY-2-BENZOFURANYL)PIPERIDINE DIHYDROBROMIDE MONOHYDRATE

To N,N-diethyl-7-methoxy-2-(1-methyl-4-piperidinyl) benzofuranamide (2.1 g) in anhydrous THF (20 ml) at room temperature was added a 1M $LiAlH_4$ solution in THF (6 ml) dropwise via syringe. The mixture was then heated to 50° C. for 3 hours and after cooling, water (0.5 ml) was carefully added. The mixture was filtered and the filter cake washed twice with ethyl acetate. The combined filtrates were dried ($Na_2SO_4$) and concentrated in vacuo to leave 1.7 g of an oil. To a solution of the oil in DCM was added an HBr solution in diethyl ether at room temperature. The resulting precipitate was filtered, washed with diethyl ether and crystallized from DCM, m.p. 226°–229° C. (dec.).
Analysis: Calculated for $C_{20}H_{30}N_2O_2 \cdot 2HBr \cdot H_2O$: 47.07% C 6.72% H 5.49% N Found: 46.78% C 6.67% H 5.33% N

EXAMPLE 7

2-(1-METHYL-4-PIPERIDINYL)-BENZOFURAN-7-YL METHYL CARBAMATE

A mixture of 1-methyl-4-(7-methoxy-2-benzofuranyl) piperidine (5.6 g) and 48% HBr (40 mi) was stirred at 120° C. for 30 minutes. After cooling to room temperature, the mixture was neutralized with 10% sodium hydroxide solution and extracted with 1:1 ethyl acetate/1-butanol. The organic extract was washed with brine, concentrated and the resulting oil was chromatographed (silica gel, eluting with 20% MeOH/DCM and 0.5% $NH_4OH$) to afford 1.9 g of 1-methyl-4-(7-hydroxy-2-benzofuranyl)piperidine.

To a mixture of 1-methyl-4-(7-hydroxy-2-benzofuranyl) piperidine (1.8 g) and a catalytic amount of CuCl in DMF (30 ml) was added methylisocyanate (0.7 ml) at room temperature under $N_2$. The mixture was then stirred for 16 hours at ambient temperature. Water and brine were added and the mixture was extracted with ethyl acetate. The organic phase was washed with brine, dried ($Na_2SO_4$) and concentrated in vacuo. Flash chromatography (silica gel, eluting with 10% MeOH/DCM+0.2% $NH_4OH$) afforded the product, which was crystallized from ethyl acetate, m.p. 144°–146° C.

Analysis: Calculated for $C_{16}H_{20}N_2O_3$: 66.65% C 6.99% H 9.72% N Found: 66.53% C 7.04% H 9.69% N

EXAMPLE 8

2-(4-PYRIDINYL)BENZOFURAN-7-YL METHYL CARBAMATE

A mixutre of 4-(7-methoxy-2-benzofuranyl)pyridine (5.0 g) and 48% HBr (50 ml) was stirred at 120° C. for 1 hour. The mixture was cooled to room temperature, neutralized with 10% NaOH and 5% $Na_2CO_3$ and extracted with ethyl acetate. The organic extract was washed with brine and concentrated to give 4-(7-hydroxy-2-benzofuranyl)pyridine.

To a mixture of 4-(7-hydroxy-2-benzofuranyl)pyridine (2.0 g) and a catalytic amount of CuCl in DCM (10 ml) and ethyl acetate (20 ml) was added methylisocyanate (1.0 ml) at room temperature under $N_2$. The mixture was stirred at ambient temperature for 16 hours, diluted with methanol, filtered through $Al_2O_3$ and concentrated in vacuo to give 2.0 g of the crude product which was crystallized from ethyl acetate, m.p. 158°–160° C.

Analysis: Calculated for $C_{15}H_{12}N_2O_3$: 67.16% C 4.51% H 10.44% N Found; 67.20% C 4.22% H 10.29% N

EXAMPLE 9

4-(7-METHOXY-2-BENZOFURANYL)-PYRIDINE

To a solution of o-vanillin (6.0 g) and 4-picolylchloride hydrochloride (6.6 g) in DMF (70 ml) was added potassium carbonate (20.0 g) and potassium iodide (2.0 g). The mixture was stirred vigorously for 8 hours at 150° C. The mixture was filtered hot and the filter cake was washed with ethyl acetate. The organic phases were combined and concentrated in vacuo to a volume of about 10 ml, poured into water and extracted twice with ethyl acetate. The combined organic layers were washed with water, dried ($Na_2SO_4$) and concentrated in vacuo. Flash chromatography (silica gel, eluting with 1:2 heptane:ethyl acetate) afforded 2.5 g of the product, which was crystallized from heptane/ethyl acetate, m.p. 140°–141° C.

Analysis: Calculated for $C_{14}H_{11}NO_2$: 74.65% C 4.92% H 6.22% N Found: 74.67% C 4.73% H 6.09% N

EXAMPLE 10

2-(4-PYRIDINYL)BENZOFURAN-7-YL BUTYL CARBAMATE

To a mixture of 4-(7-hydroxy-2-benzofuranyl)pyridine (1.1 g) and 1,8-diazabicyclo [5.4.0]undec-7-ene(150.0 mg) in acetonitrile (20 ml) was added n-butylisocyanate (0.5 g) at room temperature under $N_2$. The mixture was then stirred at ambient temperature for 3 hours. The crude product which precipitated out of the reaction mixture was filtered and crystallized from ethyl acetate, then chromatographed silica gel, 2:1 heptane/acetone) to remove residual impurities. Concentration of the appropriate fractions afforded the product, m.p. 140° C.

Analysis: Calculated for $C_{18}H_{18}N_2O_3$: 69.66% C 5.85% H 9.03% N Found: 69.27% C 5.42% H 8.96% N

EXAMPLE 11

1-METHYL-4-(7-METHOXY-2-BENZOFURANYL) PIPERIDINE

A mixture of 4-(7-methoxy-2-benzofuranyl)pyridine (66 g), methyl iodide (56.7 g) and 2-butanone (800 ml) was stirred at 50° C. for 4 hours, cooled to room temperature, filtered and the resulting solid was washed with 2-butanone to provide 1-methyl-4-(7-methoxy-2-benzofuranyl) pyridinium iodide, m.p. 225°–227° (dec.). The quaternary salt (90 g) was dissolved in methanol (1 l) and a solution of $NaBH_4$ (40 g) in $H_2O$ (250 ml) was added dropwise. The mixture was stirred at ambient temperature for 3 hours, concentrated and the residual aqueous layer was extracted with DCM. The extracts were combined, washed with brine and concentrated to give 1-methyl-4-(7-methoxy-2-benzofuranyl)-1,2,3,6-tetrahydropyridine.

A mixture of 1-methyl-4-(7-methoxy-2-benzofuranyl)-1,2,3,6-tetrahydropyridine (58.0 g), methanol (1.5 l), water (200 ml), 48% HBr (42.0 g), and platinum dioxide were shaken under hydrogen at room temperature for 6 hours. The mixture was filtered; the filtrate was concentrated in vacuo to the aqueous phase, neutralized with 5% $Na_2CO_3$ and extracted with $CH_2Cl_2$. The organic phase was washed with water, dried ($Na_2SO_4$) and concentrated in vacuo to give 59 g of the crude product, which was crystallized from methanol/water, m.p. 74°–75° C.

Analysis: Calculated for $C_{15}H_{17}NO_2$: 73.44% C 7.81% H 5.71% N Found: 73.47% C 7.83% H 5.65% N

EXAMPLE 12

2-(4-PIPERIDINYL)BENZOFURAN-7-YL DIMETHYL CARBAMATE HEMIFUMARATE

To a mixture of 1-methyl-4-(7-hydroxy-2-benzofuranyl) piperdine (3.8 g), triethylamine (1.2 g), DBU (0.3 g) in acetonitrile (20 ml) was added a solution of dimethyl cabamoyl chloride (1.4 g) in acetonitrile (10 ml). The mixture was stirred at ambient temperature overnight, concentrated and chromatographed (silica gel eluting with 10% MeOH/DCM) to afford 1.2 g of 2-(1-methyl-piperdin-7-yl) benzofuran-7-yl dimethyl carbamate after recrystalization from ethanol.

To a suspension of 2-(1-methyl-piperdin-7-yl) benzofuran-7-yl dimethyl carbamate (1.0 g) in dichloroethane (10 ml) was added chloroethyl chloroformate (0.47 g) and the mixture was refluxed for 3 hours. After stirring at room temperature overnight, an additional 0.95 gram of 2-chloroethyl chloroformate was added and the mixture refluxed for 6 hours. The mixture was concentrated, 10 ml of methanol was added and the mixture was heated to reflux for 2 hours. After concentration, the residue was chromatographed (silica gel, 10% MeOH/$CH_2CH_2$ containing 0.5% $NH_4OH$) and the fractions were evaporated. The product was dissolved in ethyl acetate and a solution of fumaric acid in ether was added; the resulting solid was collected and dried, m.p. 195°–196° C.

Analysis: Calculated for: $C_{18}H_{22}N_2O_5$ 62.42% C 6.40% H 8.09% N Found: 62.25% C 6.38% H 7.98% N

We claim:

1. A compound of the formula

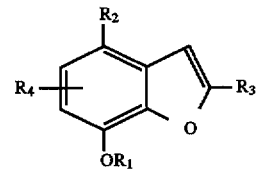

wherein $R_1$ is $CONHR_{11}$ or $CONR_6R_7$ $R_2$ is hydrogen, cyano, $CH_2NR_8R_9$, $CONHR_5$ or $CONR_6R_7$;

$R_3$ is

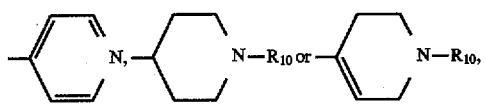

where $R_{10}$ is hydrogen, loweralkyl, arylloweralkyl, $CONHR_5$, $CONR_6R_7$, acyl, acyloxyloweralkyl or acyloxyarylloweralkyl;

$R_4$ is hydrogen, halogen, loweralkyl or loweralkoxy;

$R_5$ is hydrogen, loweralkyl or arylloweralkyl;

$R_6$ is loweralkyl or arylloweralkyl;

$R_7$ is loweralkyl or arylloweralkyl;

$R_8$ is hydrogen, loweralkyl, arylloweralkyl or acyl;

$R_9$ is hydrogen, loweralkyl or arylloweralkyl;

$R_{11}$ is loweralkyl, aryl or arylloweralkyl;

or a pharmaceutically acceptable acid addition salt thereof, or, where applicable, an optical or geometric isomer or racemic mixture thereof.

2. A compound as defined in claim 1 wherein $R_3$ is

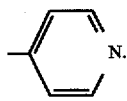

3. A compound as defined in claim 1 wherein $R_3$ is

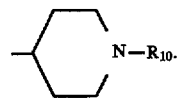

4. A compound as defined in claim 1 wherein $R_3$ is

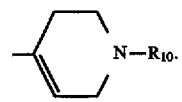

5. A compound as defined in claim 2 wherein $R_1$ is $CONHR_{11}$.

6. The compound as defined in claim 5 which is 2-(4-pyridinyl)benzofuran-7-yl methyl carbamate.

7. The compound as defined in claim 5 which is 2-(4-pyridinyl)benzofuran-7-yl butyl carbamate.

8. A compound as defined in claim 3 wherein $R_1$ is $CONHR_{11}$.

9. The compound as defined in claim 8 which is 2-(1-methyl-4-piperidinyl)benzofuran-7-yl methyl carbamate.

10. A compound as defined in claim 3 wherein $R_1$ is $CONR_6R_7$.

11. The compound as defined in claim 10 which is 2-(4-piperidinyl)-benzofuran-7-yl dimethyl carbamate.

12. A pharmaceutical composition which comprises an effective amount of a compound as defined in claim 1 and a pharmaceutically acceptable carrier therefor.

13. A method of treating memory dysfunction of the Alzheimer's type comprising administering to a patient an acetyl-cholinesterase inhibitory effective amount of a compound as defined in claim 1.

* * * * *

UNITED STATES PATENT AND TRADEMARK OFFICE
CERTIFICATE OF CORRECTION

PATENT NO. : 5,708,007

DATED : January 13, 1998

INVENTOR(S) : Gerard J. O'Malley et al.

It is certified that error appears in the above-identified patent and that said Letters Patent is hereby corrected as shown below:

"R10" at Column 4, line 39, and should read -- $R_{10}$ --.

"R10" at Column 4, line 52, and should read -- $R_{10}$ --.

"R10" at Column 4, line 66, and should read -- $R_{10}$ --.

"R10" at Column 5, line 15, and should read -- $R_{10}$ --.

"porition" at Column 7, line 18, and should read -- portion --.

"R10" at Column 7, line 20, and should read -- $R_{10}$ --.

"hemifurnarate at Column 9, line 55, and should read -- hemifumarate --.

"quantifies" at Column 10, line 5, and should read -- quantities --.

"MEHOXY" at Column 13, line 9, and should read -- METHOXY --.

"cabamoyl" at Column 16, line 29, and should -- carbamoyl --.

Signed and Sealed this

Seventh Day of December, 1999

Attest:

Q. TODD DICKINSON

*Attesting Officer*   *Acting Commissioner of Patents and Trademarks*